US008980819B2

(12) United States Patent
Aoki et al.

(10) Patent No.: US 8,980,819 B2
(45) Date of Patent: Mar. 17, 2015

(54) 4(3)-(4-HYDROXY-4-METHYLPENTYL)-3-CYCLOHEXENE-1-CARBONITRILE

(71) Applicant: Kao Corporation, Tokyo (JP)

(72) Inventors: Takashi Aoki, Wakayama (JP); Takahiro Hirose, Chiba (JP); Shoichi Tahara, Ichikawa (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/251,744

(22) Filed: Apr. 14, 2014

(65) Prior Publication Data

US 2014/0349901 A1 Nov. 27, 2014

(30) Foreign Application Priority Data

May 23, 2013 (JP) ................................ 2013-109309

(51) Int. Cl.

| | |
|---|---|
| ***A61K 8/00*** | (2006.01) |
| ***C11B 9/00*** | (2006.01) |
| ***C11D 3/50*** | (2006.01) |

(52) U.S. Cl.

CPC ................ *C11B 9/0034* (2013.01); *C11D 3/50* (2013.01)

USPC ............................................ 512/22; 558/431

(58) Field of Classification Search

USPC ............................................ 558/431; 512/22

See application file for complete search history.

(56) References Cited

FOREIGN PATENT DOCUMENTS

| | | | |
|---|---|---|---|
| GB | 1 545 171 | | 5/1979 |
| JP | 49-48945 | | 12/1974 |
| JP | 49-135948 | | 12/1974 |
| JP | 53-52635 | | 5/1978 |
| JP | 55-92349 | * | 7/1980 |

OTHER PUBLICATIONS

"Synthetic perfume Product knowledge and the chemistry", Enlarged and Revised Edition Publication, Mar. 22, 2005, 9 pages ( with Unedited Computer Generated English Translation).

Innospec, "Azuril", [online], 2008, 2 pages.

* cited by examiner

*Primary Examiner* — John Hardee

(74) *Attorney, Agent, or Firm* — Oblon, McClelland, Maier & Neustadt, L.L.P.

(57) ABSTRACT

A compound and a fragrance composition containing the same are provided, wherein the compound has a citrus odor in addition to a muguet odor, which is useful as a fragrance, is stable in an aqueous vehicle, and can provide a bright muguet odor with good fragrance retention by being blended with another fragrance. Particularly, they are 4(3)-(4-hydroxy-4-methylpentyl)-3-cyclohexene-1-carbonitrile and a fragrance composition containing 4(3)-(4-hydroxy-4-methylpentyl)-3-cyclohexene-1-carbonitrile.

19 Claims, No Drawings

4(3)-(4-HYDROXY-4-METHYLPENTYL)-3-CYCLOHEXENE-1-CARBONITRILE

FIELD OF THE INVENTION

The present invention relates to a new 4(3)-(4-hydroxy-4-methylpentyl)-3-cyclohexene-1-carbonitrile and a fragrance composition containing the same.

BACKGROUND OF THE INVENTION

Fragrance is an important element that creates, for example, preference, a sense of luxury, a sense of ease, and expectations for the effect for products and the like. Furthermore, a distinctive fragrance provides a product differentiation effect and the capacity for attracting customers. On the other hand, in order to control, for example, a long-lasting property and balance of fragrance, generally, a fragrance is imparted to a product using a fragrance composition in which a plurality of fragrance materials are mixed together. It is required for the fragrance materials composing the fragrance composition to be highly harmonious with other fragrance materials.

As a fragrance material, which is a nitrile compound with an alicyclic structure, Peonile (Givaudan), 2-cyclohexylidene-2-phenylacetonitrile, is known to have a fresh, grapefruit, geranium, rose floral-like odor (Non-Patent Document 1). Furthermore, Azuril (Innospec), 4(3)-(4-methyl-3-pentenyl)-3-cyclohexene-1-carbonitrile, is known to have a citrus-like odor (Non-Patent Document 2).

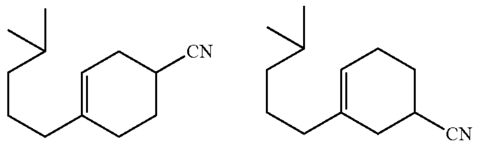

Azuril

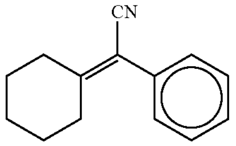

Peonile

In addition, Patent Document 1 discloses a method of producing a mixture of isomers of 3-cyano-3-methyl- and 4-cyano-4-methyl-1-(4-methyl-3-pentenyl)cyclohexane, which has a soft, floral odor and is produced by reacting myrcene with methacrylonitrile in a closed system at high temperature.

Patent Document 2 discloses a fragrance composition characterized by containing an olfactory perceptible amount of compound of dimethylcyclohexane-3-nitrile or trimethylcyclohexane-3-nitrile and a suitable carrier.

Patent Document 3 discloses that a particular cyclohexane derivative having a cyano group or a carbamoyl group has a pharmacological action such as an antiallergic action and therefore is a useful compound as a pharmaceutical agent.

Furthermore, it is known that Lyral (IFF), 4(3)-(4-hydroxy-4-methylpentyl)-3-cyclohexene-1-carboxaldehyde, has a lily of the valley like odor similar to hydroxycitronellal (Non-Patent Document 1).

Very roughly speaking, fragrance materials have similar fragrance notes when they have similar structures to each other, but there are many exceptions. Particularly, when a plurality of substituents are combined to change the fragrance note, it is difficult to predict how the fragrance note will change and it also is difficult to predict the harmonicity with other fragrance materials.

PRIOR ART DOCUMENTS

Non-Patent Document

[Non-Patent Document 1] "Gosei Koryo, Kagaku to Shohin Chishiki" (Synthetic Perfumes, Chemistry and Commodity Knowledge), authored by Genichi Indo, Enlarged and Revised Edition, 2005, pp. 198 and 702

[Non-Patent Document 2] Innospec, "Azuril", [online], 2008, [May 8, 2013], Internet http://www.innospecinc.com/assets/_files/documents/apr__08/cm__1209462136_Azuril-Citrus.pdf

Patent Documents

[Patent Document 1] JP 49(1974)-48945 B

[Patent Document 2] JP 53(1978)-52635 A

[Patent Document 3] JP 55(1980)-92349 A

SUMMARY OF THE INVENTION

Fragrance materials are required to provide, for example, products with desirable preference, etc. as described above. Particularly, muguet (lily of the valley) is an important odor with a floral tone, and there are demands for one having a secondary odor to express a further complex fragrance note. Furthermore, there are demands for fragrance materials that are excellent in blendability with respect to products, stability, and long-lasting property.

Therefore, with the foregoing in mind, it is an object of the present invention to provide a compound and a fragrance composition containing the same, wherein the compound has a citrus odor in addition to a muguet odor, which is useful as a fragrance, is stable in an aqueous vehicle, and can provide a bright muguet odor with good fragrance retention by being blended with another fragrance.

DETAILED DESCRIPTION OF THE INVENTION

The present inventors found that 4(3)-(4-hydroxy-4-methylpentyl)-3-cyclohexene-1-carbonitrile had a citrus odor in addition to a muguet odor, was stable in an aqueous vehicle, and was able to provide a bright muguet odor with good fragrance retention by being blended with another fragrance, and thereby completed the present invention.

In other words, the present invention provides 4(3)-(4-hydroxy-4-methylpentyl)-3-cyclohexene-1-carbonitrile.

Furthermore, the present invention provides a fragrance composition containing 4(3)-(4-hydroxy-4-methylpentyl)-3-cyclohexene-1-carbonitrile.

4(3)-(4-Hydroxy-4-methylpentyl)-3-cyclohexene-1-carbonitrile of the present invention has a citrus odor in addition to a muguet odor, which is useful as a fragrance, and is stable in an aqueous vehicle. Moreover, 4(3)-(4-hydroxy-4-methylpentyl)-3-cyclohexene-1-carbonitrile of the present invention can provide a bright muguet odor with good fragrance retention by being blended with another fragrance.

The present invention provides 4(3)-(4-hydroxy-4-methylpentyl)-3-cyclohexene-1-carbonitrile. In the present specification, the "4(3)-(4-hydroxy-4-methylpentyl)-3-cyclohexene-1-carbonitrile" denotes a mixture of both isomers of "4-(4-hydroxy-4-methylpentyl)-3-cyclohexene-1-carbonitrile"

and "3-(4-hydroxy-4-methylpentyl)-3-cyclohexene-1-carbonitrile". The mixing ratio of the mixture is not particularly limited, but, for example, when either one of the 4-(4-hydroxy-4-methylpentyl)-3-cyclohexene-1-carbonitrile and the 3-(4-hydroxy-4-methylpentyl)-3-cyclohexene-1-carbonitrile is considered as a main component while the other is considered as an accessory component, the ratio between the main component and the accessory component is 1 to 100:1. Alternatively, the 4-(4-hydroxy-4-methylpentyl)-3-cyclohexene-1-carbonitrile and the 3-(4-hydroxy-4-methylpentyl)-3-cyclohexene-1-carbonitrile may be contained at a ratio of 1:1. The chemical structures of the "4-(4-hydroxy-4-methylpentyl)-3-cyclohexene-1-carbonitrile" and the "3-(4-hydroxy-4-methylpentyl)-3-cyclohexene-1-carbonitrile" are as shown in Formula (IA) and Formula (IB) below, respectively.

(IA)

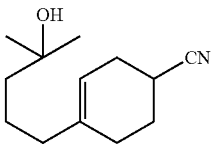

4-(4-Hydroxy-4-methylpentyl)-3-cyclohexene-1-carbonitrile (IB)

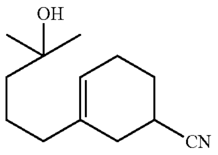

3-(4-Hydroxy-4-methylpentyl)-3-cyclohexene-1-carbonitrile

Furthermore, in the present specification, for the sake of convenience, "4(3)-(4-hydroxy-4-methylpentyl)-3-cyclohexene-1-carbonitrile" is represented by Formula (I) below. That is, the compound of Formula (I) is a mixture of a compound of Formula (IA) above and a compound of Formula (IB) above.

(I)

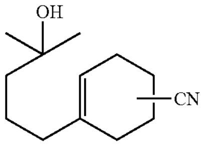

Method of Producing 4(3)-(4-Hydroxy-4-Methylpentyl)-3-Cyclohexene-1-Carbonitrile 4(3)-(4-Hydroxy-4-methylpentyl)-3-cyclohexene-1-carbonitrile of the present invention can be synthesized using a general organic chemical reaction and the method for producing it is not limited. A preferable method for producing 4(3)-(4-hydroxy-4-methylpentyl)-3-cyclohexene-1-carbonitrile of the present invention is, for example, a method including a dehydration step in which 4(3)-(4-hydroxy-4-methylpentyl)-3-cyclohexene-1-carboxaldehyde oxime (hereinafter, also referred to as an "oxime intermediate" in the present specification) is dehydrated to yield 4(3)-(4-hydroxy-4-methylpentyl)-3-cyclohexene-1-carbonitrile.

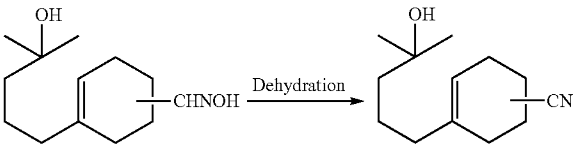

(II) (I)

Formula (II) above represents 4(3)-(4-hydroxy-4-methylpentyl)-3-cyclohexene-1-carboxaldehyde oxime and denotes a mixture of 4-(4-hydroxy-4-methylpentyl)-3-cyclohexene-1-carboxaldehyde oxime and 3-(4-hydroxy-4-methylpentyl)-3-cyclohexene-1-carboxaldehyde oxime. The chemical structures of the "4-(4-hydroxy-4-methylpentyl)-3-cyclohexene-1-carboxaldehyde oxime" and the "3-(4-hydroxy-4-methylpentyl)-3-cyclohexene-1-carboxaldehyde oxime" are as shown in Formula (IIA) and Formula (IIB) below, respectively. In the present specification, for the sake of convenience, "4(3)-(4-hydroxy-4-methylpentyl)-3-cyclohexene-1-carboxaldehyde oxime" is represented by Formula (II) below. That is, a compound of Formula (II) is a mixture of a compound of Formula (IIA) below and a compound of Formula (IIB) below.

(IIA)

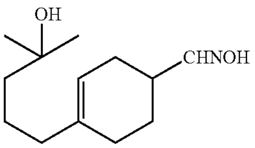

4-(4-Hydroxy-4-methylpentyl)-3-cyclohexene-1-carboxaldehyde oxime (IIB)

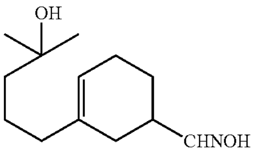

3-(4-Hydroxy-4-methylpentyl)-3-cyclohexene-1-carboxaldehyde oxime (II)

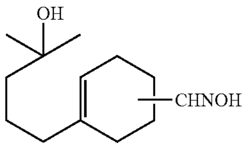

Preferably, the above-mentioned oxime intermediate is produced by, for example, a step of oximating 4(3)-(4-hydroxy-4-methylpentyl)-3-cyclohexene-1-carboxaldehyde to yield 4(3)-(4-hydroxy-4-methylpentyl)-3-cyclohexene-1-carboxaldehyde oxime (the oxime intermediate).

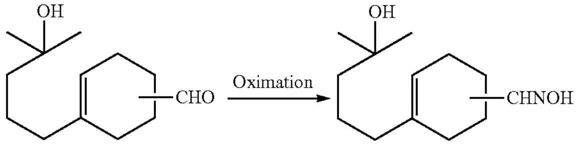

(III) (II)

Formula (III) above represents 4(3)-(4-hydroxy-4-methylpentyl)-3-cyclohexene-1-carboxaldehyde and denotes a mixture of 4-(4-hydroxy-4-methylpentyl)-3-cyclohexene-1-carboxaldehyde and 3-(4-hydroxy-4-methylpentyl)-3-cyclohexene-1-carboxaldehyde. The chemical structures of the "4-(4-hydroxy-4-methylpentyl)-3-cyclohexene-1-carboxaldehyde" and the "3-(4-hydroxy-4-methylpentyl)-3-cyclohexene-1-carboxaldehyde" are as shown in Formula (IIIA) and Formula (IIIB) below, respectively. In the present specification, for the sake of convenience, "4(3)-(4-hydroxy-4-methylpentyl)-3-cyclohexene-1-carboxaldehyde" is represented by Formula (III) below. In other words, a compound of Formula (III) is a mixture of a compound of Formula (IIIA) below and a compound of Formula (IIIB) below.

(IIIA)

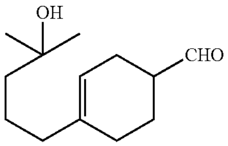

4-(4-Hydroxy-4-methylpentyl)-3-cyclohexene-1-carboxaldehyde (IIIB)

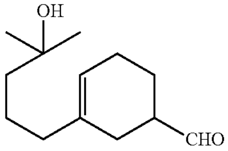

3-(4-Hydroxy-4-methylpentyl)-3-cyclohexene-1-carboxaldehyde (III)

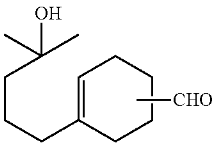

4(3)-(4-Hydroxy-4-methylpentyl)-3-cyclohexene-1-carboxaldehyde can be produced according to known documents. Examples of available commercial products of 4(3)-(4-hydroxy-4-methylpentyl)-3-cyclohexene-1-carboxaldehyde include "Lyral" (Trade Name) manufactured by IFF.

<Dehydration Step>

As described above, the production method of the present invention includes a step of dehydrating 4(3)-(4-hydroxy-4-methylpentyl)-3-cyclohexene-1-carboxaldehyde oxime (an oxime intermediate) to yield 4(3)-(4-hydroxy-4-methylpentyl)-3-cyclohexene-1-carbonitrile.

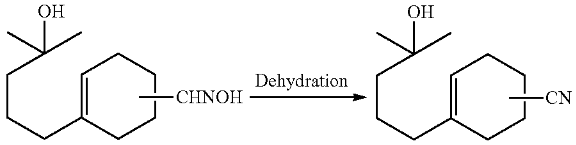

(II) (I)

Preferably, this step is carried out by, for example, an acetic anhydride method using acetic anhydride or an alkali catalyst method using alkali. From the viewpoint of increasing the yield and the purity of the product to be obtained, the alkali catalyst method is more preferable.

[Acetic Anhydride Method]

The acetic anhydride method includes a step of dehydrating 4(3)-(4-hydroxy-4-methylpentyl)-3-cyclohexene-1-carboxaldehyde oxime (an oxime intermediate) by heating in the presence of acetic anhydride to yield 4(3)-(4-hydroxy-4-methylpentyl)-3-cyclohexene-1-carbonitrile.

From the viewpoints of increasing the yield and the simplicity of the post-reaction treatment, the amount of the acetic anhydride to be used in the acetic anhydride method is preferably 1.0 to 10 times by mole, more preferably 1.0 to 5 times by mole, and further preferably 1.0 to 1.5 times by mole, with respect to the amount of the oxime intermediate.

From the viewpoint of completing the reaction efficiently, the reaction temperature is preferably 120 to 200° C., at which unreacted acetic anhydride and by-product acetic acid are refluxed sufficiently, more preferably 120 to 180° C., and further preferably 120 to 160° C.

The reaction can be carried out in the absence of a solvent. However, from the viewpoint of gradual heating, the reaction can be carried out under reflux using a suitable amount of solvent having a boiling point around the preferred reaction temperature.

A reaction product, 4(3)-(4-hydroxy-4-methylpentyl)-3-cyclohexene-1-carbonitrile, as well as excess acetic anhydride and by-product acetic acid can be separated by a method in which after reaction, they are distilled and neutralized with alkaline water to be acetate, which then is removed together with an aqueous layer.

[Alkali Catalyst Method]

The alkali catalyst method includes a step of dehydrating 4(3)-(4-hydroxy-4-methylpentyl)-3-cyclohexene-1-carboxaldehyde oxime (an oxime intermediate) by heating in the presence of an alkali catalyst to yield 4(3)-(4-hydroxy-4-methylpentyl)-3-cyclohexene-1-carbonitrile.

In the alkali catalyst method, a hydroxide of alkali metal such as sodium hydroxide or potassium hydroxide is used preferably as the alkali catalyst.

The amount of the alkali catalyst to be used is preferably 0.1 to 20 mass % with respect to the oxime intermediate from the viewpoint of increasing the yield and more preferably 1 to 15 mass % from the viewpoint of the reaction controllability.

In the alkali catalyst method, it is preferable that the reaction be carried out while by-product water is removed out of the system. Examples of such a method include an azeotropic dehydration method that is carried out under solvent reflux and a continuous dehydration method in which the product also is removed out of the reaction system. Among them, from the viewpoint of inhibiting pyrolysis and thermal polymerization of 4(3)-(4-hydroxy-4-methylpentyl)-3-cyclohexene-1-carbonitrile that is obtained as a product, the continuous dehydration method is preferred in which 4(3)-(4-hydroxy- 4-methylpentyl)-3-cyclohexene-1-carbonitrile also is removed out of the reaction system.

The reaction temperature employed in the alkali catalyst method is preferably 80 to 250° C. from the viewpoints of completing the reaction efficiently and inhibiting pyrolysis and thermal polymerization of an oxime intermediate and 4(3)-(4-hydroxy-4-methylpentyl)-3-cyclohexene-1-carbonitrile and is more preferably 120 to 200° C. from the viewpoint of increasing the yield. In this case, from the viewpoints of distilling 4(3)-(4-hydroxy-4-methylpentyl)-3-cyclohexene-1-carbonitrile efficiently in the preferable temperature range and inhibiting pyrolysis and thermal polymerization of the product, it is carried out preferably under reduced pressure and more preferably at 10 kPa or lower.

Furthermore, from the viewpoint of shortening the retention time of the oxime intermediate to inhibit side reactions, a preferred method is one in which the oxime intermediate is dropped continuously into the reaction system.

From the viewpoint of improving the quality of 4(3)-(4-hydroxy-4-methylpentyl)-3-cyclohexene-1-carbonitrile obtained by either one of the methods so that it has a more preferable quality as a fragrance material, it is preferable that further distillation and silica gel column chromatography purification be carried out.

Hereinafter, an example of the production method is described in which the above-mentioned oxime intermediate is obtained according to the production method of the present invention.

<Oximation Step>

For example, the oximation reaction can be carried out using 4(3)-(4-hydroxy-4-methylpentyl)-3-cyclohexene-1-carboxaldehyde and hydroxylamine to yield 4(3)-(4-hydroxy-4-methylpentyl)-3-cyclohexene-1-carboxaldehyde oxime (an oxime intermediate).

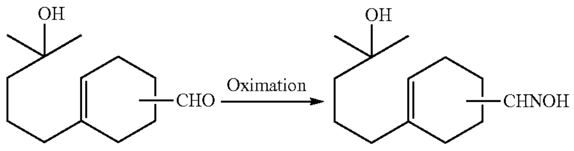

(III) (II)

Examples of suitable methods to be used in this step include a method of dropping a hydroxylamine aqueous solution into 4(3)-(4-hydroxy-4-methylpentyl)-3-cyclohexene-1-carboxaldehyde and a method of dropping a base into a mixture of 4(3)-(4-hydroxy-4-methylpentyl)-3-cyclohexene-1-carboxaldehyde and an aqueous solution of an inorganic acid salt of hydroxylamine. Particularly, the later is preferable in which a base is dropped into a mixture of 4(3)-(4-hydroxy-4-methylpentyl)-3-cyclohexene-1-carboxaldehyde and an aqueous solution of an inorganic acid salt of hydroxylamine. According to this method, there are advantages that dropping a base allows hydroxylamine to be produced in the reaction system, side reactions can be inhibited, and thus the reaction can be carried out safely.

From the viewpoints of inhibition of the side reactions and economic efficiency, it is preferable to use hydroxylamine sulfate as the inorganic acid salt of hydroxylamine used in this step.

From the viewpoints of simplicity in the post-reaction treatment and economic efficiency, the amount of the hydroxylamine or an inorganic acid salt thereof to be used is, in terms of hydroxylamine, preferably 1.0 to 3.0 times by mole, more preferably 1.0 to 2.0 times by mole, and further preferably 1.0 to 1.5 times by mole, with respect to 4(3)-(4-hydroxy-4-methylpentyl)-3-cyclohexene-1-carboxaldehyde.

The base used in a suitable method of dropping the base is one of stronger bases than hydroxylamine and particularly it is preferably water soluble. From an economic perspective, preferable examples are alkali metal hydroxides such as sodium hydroxide and potassium hydroxide. From the viewpoints of handleability and operating efficiency, it is preferable to use an aqueous solution containing 20 to 40 mass % of alkali metal hydroxide.

The reaction can be carried out in the absence of a solvent. However, from the viewpoint of inhibiting the increase in viscosity of the reaction solution that is caused by gradual heating and the development of the reaction, it is preferable to use a solvent. Examples of preferable solvents include aliphatic alcohol and water that easily dissolve an aldehyde intermediate and hydroxylamine, which are the starting materials. The aliphatic alcohol is preferably aliphatic alcohol having 1 to 3 carbon atoms, more preferably, for example, ethanol or isopropyl alcohol. The above-mentioned solvent is more preferably a mixture of aliphatic alcohol and water.

From the viewpoints of completing the reaction efficiently and inhibiting exothermic decomposition of hydroxylamine, it is preferable that the reaction temperature be maintained at 30° C. to 50° C.

The oxime intermediate, which is a reaction product, can be used for the subsequent reaction without further being processed after an aqueous layer is separated therefrom. Preferably, however, it is used after the solvent and a byproduct with a high boiling point are removed by, for example, distillation purification.

[Fragrance Composition]

The fragrance composition of the present invention contains 4(3)-(4-hydroxy-4-methylpentyl)-3-cyclohexene-1-carbonitrile. The amount of 4(3)-(4-hydroxy-4-methylpentyl)-3-cyclohexene-1-carbonitrile contained in the fragrance composition is preferably 0.01 to 99 mass %, more preferably 0.1 to 15 mass %, and further preferably 0.3 to 3 mass %. When it contains 0.01 to 99 mass % of 4(3)-(4-hydroxy-4-methylpentyl)-3-cyclohexene-1-carbonitrile, the fragrance composition can be provided with a bright muguet odor with good fragrance retention.

Since the fragrance composition of the present invention contains 4(3)-(4-hydroxy-4-methylpentyl)-3-cyclohexene-1-carbonitrile, it has muguet and citrus odors and can be blended with another fragrance to be provided with a bright muguet odor with good fragrance retention. Furthermore, the fragrance composition of the present invention is allowed to contain, as another fragrance, another fragrance component that is generally used or a blended fragrance having a desired composition in addition to 4(3)-(4-hydroxy-4-methylpentyl)-3-cyclohexene-1-carbonitrile and thereby can be provided with an odor with, for example, a citrus tone, a floral tone, a fruity tone, a herbal tone, a spicy tone, a green tone, a woody tone, or a balsam tone.

In the fragrance composition of the present invention, the another fragrance that can be used to be combined with 4(3)-(4-hydroxy-4-methylpentyl)-3-cyclohexene-1-carbonitrile is preferably at least one selected from hydrocarbons, alcohols, phenols, aldehydes, ketones, acetals, ethers, esters, carbonates, lactones, oximes, nitriles, Schiff bases, nitrogen-containing compounds, sulfur-containing compounds, natural essential oils, and natural extracts. Particularly, at least one selected from alcohols, aldehydes, ketones, ethers, esters, lactones, and natural essential oils is more preferable from the viewpoint of enhancing the freshness and diffusibility by being blended with another fragrance.

Hereinafter, the "plural notation" of each fragrance denotes a single compound or a mixture of at least two compounds.

Examples of hydrocarbons include limonene, α-pinene, β-pinene, terpinene, p-cymene, cedrene, longifolene, valencene, camphene, and myrcene.

Examples of alcohols include aliphatic alcohols, terpene-based alcohols, and aromatic alcohols.

Examples of aliphatic alcohols include prenol, trans-2-hexenol, cis-3-hexenol, 2,6-dimethylheptanol, 1-octen-3-ol, 3,6-nonadiene-1-ol, 3,6-nonadienol, Undecavertol (Trade Name of Givaudan, 4-methyl-3-decene-5-on, 2,4-dimethyl-3-cyclohexene-1-methanol, isocyclogeraniol, 2-tert-butylcyclohexanol, 4-tert-butylcyclohexanol, Mayol (Trade Name of Firmenich, 4-(1-methylethyl)-cyclohexanemethanol), Amber Core (Trade Name of Kao Corporation), Timberol (Trade Name of Symrise, 1-(2,2,6-trimethylcyclohexyl) hexan-3-ol), Sandalmysore Core (Trade Name of Kao Corporation, 2-methyl-4-(2,2,3-trimethyl-3-cyclopenten-1-yl)-2-buten-1-on, Bacdanol (Trade Name of IFF, 2-ethyl-4-(2,2,3-trimethyl-3-cyclopenten-1-yl)-2-buten-1-ol), and Florosa (Trade Name of Givaudan, 4-methyl-2-(2-methylpropyl)tetrahydro-2H-4-pyranol). Among them, cis-3-hexenol, Undecavertol, Mayol, or Florosa is preferable from the viewpoint of enhancing the freshness and diffusibility by being blended with another fragrance.

Examples of terpene-based alcohols include citronellol, hydroxycitronellol, linalool, dihydrolinalool, tetrahydrolinalool, ethyllinalool, geraniol, nerol, tetrahydrogeraniol, myrcenol, dihydromyrcenol, tetrahydromyrcenol, ocimenol, terpineol, menthol, borneol, fenchyl alcohol, farnesol, nerolidol, cedrol, and terpineol. Among them, citronellol, tetrahydrolinalool, ethyllinalool, geraniol, dihydromyrcenol, borneol, or terpineol is preferable from the viewpoint of enhancing the freshness and diffusibility by being blended with another fragrance.

Examples of aromatic alcohols include benzyl alcohol, styralyl alcohol, phenethyl alcohol, cumin alcohol, dimethyl phenyl ethyl carbinol, cinnamic alcohol, Phenyl Hexanol (Trade Name of Kao Corporation), Pamplefleur (Trade Name of IFF, 4-phenylpentanol), and Majantol (Trade Name of Symrise, 2,2-dimethyl-3-(3-methylphenyl)propanol).

Examples of phenols include anethole, guaiacol, eugenol, isoeugenol, and moss synth.

Examples of aldehydes include aliphatic aldehyde, terpene aldehyde, and aromatic aldehyde as in the case of the aforementioned alcohols. All the aldehydes in which only the alcohol group of the fragrance component alcohols has been converted to aldehyde group are included in the examples of the fragrance components.

Examples of other aldehydes include Aldehyde C-6 (Trade Name of Kao Corporation, 1-hexanal), Aldehyde C-8 (Trade Name of Kao Corporation, 1-octanal), Aldehyde C-9 (Trade Name of Kao Corporation, 1-nonanal), Aldehyde C-10 (Trade Name of Kao Corporation, 1-decanal), Aldehyde C-11 UNDECYL (Trade Name of Kao Corporation, undecanal), Aldehyde C-111 LEN (Trade Name of Kao Corporation, 10-undecenal), Aldehyde C-12 LAURYL (Trade Name of Kao Corporation, 1-dodecanal), Aldehyde C-12 MNA (Trade Name of Kao Corporation, 2-methyl-undecanal), cis-4-decenal, trans-4-decenal, Floral Super (Trade Name of IFF, 4,8-dimethyl-4,9-decadienal), Pollenal II (Trade Name of Kao Corporation, 2-cyclohexylpropanal), Myrac Aldehyde (Trade Name of IFF, 4(3)-(4-methyl-3-pentene-1-yl)-3-cyclohexene-1-carboxaldehyde), LYRAL (Trade Name of IFF, 4(3)-(4-hydroxy-4-methylpentyl)-3-cyclohexene-1-carboxaldehyde), Cetonal (Trade Name of Givaudan, trimethyl cyclohexen methylbutanal), Vernaldehyde (Trade Name of Givaudan, 1-methyl-4-(4-methylpentyl)-3-cyclohexenecarbaldehyde), Melozone (Trade Name of IFF, octahydro-4,7-methanoindenecarboxaldehyde), Scentenal (Trade Name of Firmenich, methoxydicyclopentadienecarboxaldehyde), Dupical (Trade Name of Givaudan, 4-tricyclodecylidenebutanal), Bergamal (Trade Name of IFF, 3,7-dimethyl-2-methylene-6-octenal), campholenic aldehyde, Bourgeonal (Trade Name of Givaudan, 3-(4-tert-butylphenyl)propanal), Cyclamen Aldehyde (Trade Name of Givaudan, 3-(4-isopropylphenyl)-2-methylpropionaldehyde), Floralozone (Trade Name of IFF, 3-(4-ethylphenyl)-2,2-dimethylpropionaldehyde), Suzaral (Trade Name of Takasago International Corporation, 3-(4-isobutylphenyl)-2-methylpropionaldehyde), Lilial (Trade Name of Givaudan, 3-(4-t-butylphenyl)-2-methyl propionaldehyde), Amyl Cinnamic Aldehyde (Trade Name of Kao Corporation), Hexyl Cinnamic Aldehyde (Trade Name of Kao Corporation, 2-n-hexyl-3-phenyl-2-propenal), Canthoxal (Trade Name of IFF, 2-methyl-3-(4-methoxyphenyl) propanal), vanillin, ethyl vanillin, Heliotropine (Trade Name of Takasago International Corporation, 3,4-methylenedioxybenzaldehyde), Helional (Trade Name of IFF, α-methyl-1,3-benzodioxole-5-propanal), Triplal (Trade Name of IFF, 2,4-dimethyl-3-cyclohexene-1-carboxaldehyde), and 2,6-nonadienal. Among them, Aldehyde C-12 MNA or Triplal is preferable from the viewpoint of enhancing the freshness and diffusibility by being blended with another fragrance.

Examples of ketones include methyl heptenone, dimethyl octenone, 3-octanone, hexylcyclopentanone, dihydrojasmone, Veloutone (Trade Name of Firmenich, 2,2,5-trimethyl-5-pentylcyclopentanone), Nectaryl (Trade Name of Givaudan, 2-(2-(4-methyl-3-cyclohexen-1-yl)propyl)cyclopentanone), ionone, methylionone, γ-methylionone, damascone, α-damascone, β-damascone, δ-damascone, Isodamascone (Trade Name of Symrise, 1-(2,4,4-trimethyl-2-cyclohexyl)-trans-2-butanone), damascenone, Dynascone (Trade Name of Firmenich, 1-(5,5-dimethyl-1-cyclohexen-1-yl)-4-penten-1-one), irone, Cashmeran (Trade Name of IFF, 1,2,3,5,6,7-hexahydro-1,1,2,3,3-pentamethyl-4H-inden-4-one), Iso E Super (Trade Name of IFF, 1-(1,2,3,4,5,6,7,8-octahydro-2,3,8,8-tetramethyl-2-naphthalenyl)-ethan-1-one), Calone (Trade Name of Firmenich, 7-methyl-3,4-dihydro-2H-benzodioxepin-3-one), carvone, menthone, acetyl cedrene, isolongifolanone, nootkatone, benzyl acetone, raspberry ketone, benzophenone, Tonalid (Trade Name of PFW, 6-acetyl-1,1,2,4,4,7-hexamethyl tetrahydronaphthalene), β-methyl naphthyl ketone, ethyl maltol, camphor, muscone, Muscenone (Trade Name of Firmenich, 3-methyl-5-cyclopentadecen-1-one), civetone, Globanone (Trade Name of Symrise, 8-cyclohexadecenone), and methyl nonyl ketone. Among them, γ-methylionone, β-damascone, Iso E Super, benzyl acetone, or methyl nonyl ketone is preferable from the viewpoint of enhancing the freshness and diffusibility by being blended with another fragrance.

Examples of acetals include Anthoxan (Trade Name of Kao Corporation), Boisambrene Forte (Trade Name of Kao Corporation), Troenan (Trade Name of Kao Corporation), Methyl Pamplemousse (Trade Name of Givaudan, 1,1-dimethoxy-2,2,5-trimethyl-4-hexene), acetaldehyde ethyl linalyl acetal, citral dimethyl acetal, hydratropaldehyde dimethyl acetal, Verdoxan (Trade Name of Kao Corporation), and Floropal (Trade Name of Symrise, 2,4,6-trimethyl-4-phenyl-1,3-dioxane).

Examples of ethers include Herbavert (Trade Name of Kao Corporation, 3,3,5-trimethylcyclohexyl ethyl ether), cedryl methyl ether, Ambroxan (Trade Name of Kao Corporation, [3aR-(3aα,5aβ,9aα,9bβ)]dodecahydro-3a,6,6,9a-tetramethyl naphto[2,1-b]furan), Ambrotech (Trade Name of Kao Corporation, dodecahydro-3a,6,6,9a-tetramethylnaphtho[2,1-b]furan), methyl isoeugenol, citronellyl ethyl ether, geranyl ethyl ether, 1,8-cineole, rose oxide, dihydro rose oxide, linalool oxide, estragole, anethole, hinokitiol, diphenyl oxide, β-naphthol methyl ether, β-naphthol ethyl ether, and Galaxolide (Trade Name of IFF, 1,3,4,6,7,8-hexahydro-4,6,6,7,8,8-hexamethylcyclopenta-γ-2-benzopyran). Among them, Ambrotech or diphenyl oxide is preferable from the viewpoint of enhancing the freshness and diffusibility by being blended with another fragrance.

Examples of esters to be used as a fragrance material include aliphatic carboxylic acid ester, aromatic carboxylic acid ester, and other carboxylic acid esters.

Examples of aliphatic carboxylic acids that form aliphatic carboxylic acid ester include linear and branched carboxylic acids having 1 to 18 carbon atoms. Among them, carboxylic acids having 1 to 6 carbon atoms such as formic acid, acetic acid, and propionic acid are important, and particularly acetic acid is important. Examples of aromatic carboxylic acids that form aromatic carboxylic acid ester include benzoic acid, anisic acid, phenylacetic acid, cinnamic acid, salicylic acid, and anthranilic acid. Examples of alcohols that form aliphatic and aromatic esters include linear and branched aliphatic alcohols having 1 to 5 carbon atoms and the above-mentioned fragrance component alcohols.

Examples of other carboxylic acid esters include Ethyl Safranate (Trade Name of Givaudan, ethyl dihydrocyclo geranate), Poirenate (Trade Name of Kao Corporation, ethyl-2-cyclohexyl propionate), Fruitate (Trade Name of Kao Corporation, ethyl tricyclo[$5.2.1.0^{2,6}$]decan-2-carboxylate), methyl jasmonate, MDJ (Trade Name of Kao Corporation, methyl dihydrojasmonate, methyl (2-pentyl-3-oxocyclopentyl)acetate), and Cyclohexyl Salicylate (Trade Name of Kao Corporation).

Examples of carbonates include Liffarome (Trade Name of IFF, cis-3-hexenyl methyl carbonate), Jasmacyclat (Trade Name of Kao Corporation), and Floramat (Trade Name of Kao Corporation).

Examples of lactones include γ-nonalactone, γ-decalactone, δ-decalactone, Jasmolactone (Trade Name of Firmenich, tetrahydro-6-(3-pentenyl)-2H-pyran-2-one), γ-undecalactone, coumarin, octahydrocoumarin, Florex (Trade Name of Firmenich, 6-ethylideneoctahydro-5,8-methano-2H-1-benzopyran-2-one), cyclopentadecanolide, Habanolide (Trade Name of Firmenich, 12(11)-oxacyclohexadecen-2-one), Ambrettolide (Trade Name of IFF, 10-octacycloheptadecen-2-one), and ethylene brassylate. Among them, γ-undecalactone or coumarin is preferable from the viewpoint of enhancing the freshness and diffusibility by being blended with another fragrance.

Examples of oximes include Buccoxime (Trade Name of Symrise, 1,5-dimethyl-bicyclo[3,2,1]octan-8-one oxime), Labienoxime (Trade Name of Givaudan, 2,4,4,7-tetramethyl-6,8-nonadiene-3-one oxime), and 5-methyl-3-heptanone oxime.

Examples of nitriles include dodecanenitrile, citronellyl nitrile, cuminyl nitrile, cinnamyl nitrile, and Peonile (Trade Name of Givaudan, 2-cyclohexylidene-2-phenylacetonitrile). Among them, Peonile is preferable from the viewpoint of enhancing the freshness and diffusibility by being blended with another fragrance.

Examples of Schiff bases include Aurantiol (Trade Name of Givaudan, methyl N-(3,7-dimethyl-7-hydroxyoctylidene)-anthranilate), Ligantral (Trade Name of Givaudan, methyl (3,5-dimethyl-3-cyclohexene-1-yl)methyleneanthranilate), and methyl 2-[(2-methylundecylidene)amino]benzoate.

Examples of the nitrogen-containing compounds include amides, pyrroles, indoles, and thiazoles.

Examples of amides include Gardamide (Trade Name of Givaudan, N, 2-dimethyl-N-phenylbutyramide) and Paradisamide (Trade Name of Givaudan, 2-ethyl-N-methyl-N-(3-methylphenyl)butanamide).

Examples of the sulfur-containing compounds include thiols, sulfides, thiophenes, and thiocarboxylic acids.

Examples of the natural essential oils and the natural extracts include orange, lemon, lime, bergamot, petitgrain, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamon, cedar, cypress, vetiver, patchouli, lemongrass, labdanum, galbanum, and olibanum. Among them, rosemary is preferable from the viewpoint of enhancing the freshness and diffusibility by being blended with another fragrance.

The amount of these other fragrances to be contained can be selected suitably depending on, for example, the type of the blended fragrance as well as the type and intensity of intended odor. However, the amount of each of them contained in the fragrance composition is preferably 0.0001 to 99.99 mass %, more preferably 0.001 to 80 mass %. The total amount of them contained in the fragrance composition is preferably 5 to 99.99 mass %, more preferably 50 to 99.9 mass %.

The fragrance composition of the present invention can contain an oil, which itself has no odor, to be used as a base that allows 4(3)-(4-hydroxy-4-methylpentyl)-3-cyclohexene-1-carbonitrile of the present invention and other fragrance materials to be contained therein. Such an oil allows a fragrance component to be mixed uniformly, to be easily mixed into a product, and to be easily provided with a suitable intensity of fragrance. Examples of the oil include polyhydric alcohols such as ethylene glycol, propylene glycol, butylene glycol, and dipropylene glycol, esters such as isopropyl myristate, dibutyl adipate, and diethyl sebacate, hydrocarbons such as liquid paraffin and squalane, and surfactants such as polyoxyethylene alkyl ether and sorbitan fatty acid ester.

Among them, from the viewpoint of the solubility of all the fragrance components, the oil is preferably polyhydric alcohol or ester, more preferably dipropylene glycol or isopropyl myristate. The amount of such an oil to be contained in the fragrance composition is preferably 0.01 to 95 mass %, more preferably 1 to 90 mass %, and further preferably 5 to 80 mass %.

The fragrance composition of the present invention also has an effect of being capable of providing a bright muguet odor with good fragrance retention by further being blended with another fragrance in addition to the odor of 4(3)-(4-hydroxy-4-methylpentyl)-3-cyclohexene-1-carbonitrile. Such a fragrance composition can be used suitably to provide fragrances for cleanser compositions, softener compositions, cosmetics, etc.

[Use as Fragrance Component]

The fragrance composition containing 4(3)-(4-hydroxy-4-methylpentyl)-3-cyclohexene-1-carbonitrile of the present invention is provided with muguet and citrus odors and can be used, as a fragrance component for various types of products, as a blended fragrance that has a preferable fragrance note that can provide a bright muguet odor with good fragrance retention by further being blended with another fragrance. Therefore, it is an object of the present invention to provide a method of using 4(3)-(4-hydroxy-4-methylpentyl)-3-cyclohexene-1-carbonitrile as a fragrance component, preferably a method of using 4(3)-(4-hydroxy-4-methylpentyl)-3-cyclohexene-1-carbonitrile as a fragrance component for a fragrance composition, a cleanser composition, a cosmetic, or a softener composition. For the method of using said compound, it can be contained, alone or in combination with other components, in the bases of toiletry products such as soaps, cosmetics, hair cosmetics, detergents, softeners, spray products, air fresheners, perfumes, and bath agents.

Particularly, since 4(3)-(4-hydroxy-4-methylpentyl)-3-cyclohexene-1-carbonitrile of the present invention is stable in an aqueous vehicle and can be used to provide a bright muguet odor with good fragrance retention by being blended with another fragrance, it is used, as a fragrance component, more preferably for cleanser compositions, cosmetics, and softener compositions, further preferably for cleanser compositions.

Accordingly, the present invention also provides a cleanser composition containing a fragrance composition of the present invention, a cosmetic containing a fragrance composition of the present invention, and a softener composition containing a fragrance composition of the present invention.

The cleanser composition of the present invention is preferably a body cleanser composition, a cleanser composition for clothing, and a cleanser composition for hard surfaces, more preferably a body cleanser composition and a cleanser composition for clothing, and further preferably a cleanser composition for clothing.

Examples of the body cleanser composition include a skin cleanser composition and a hair cleanser composition and it is preferably a skin cleanser composition.

Examples of the cleanser composition for hard surfaces include an all purpose cleaner and a cleanser composition for tableware.

A fabric treatment composition of the present invention is preferably a softener composition.

The cosmetic of the present invention is preferably a perfume.

It is preferable that the cleanser composition of the present invention contain an anionic surfactant in addition to 4(3)-(4-hydroxy-4-methylpentyl)-3-cyclohexene-1-carbonitrile of the present invention or a fragrance composition containing 4(3)-(4-hydroxy-4-methylpentyl)-3-cyclohexene-1-carbonitrile. Furthermore, a nonionic surfactant, a pH adjuster, a viscosity modifier, a solvent, an oil, a preservative, water, etc. can be blended thereinto.

It is preferable that the softener composition of the present invention contain a cationic surfactant in addition to 4(3)-(4-hydroxy-4-methylpentyl)-3-cyclohexene-1-carbonitrile of the present invention or a fragrance composition containing 4(3)-(4-hydroxy-4-methylpentyl)-3-cyclohexene-1-carbonitrile. Furthermore, a pH adjuster, a solvent, an oil, a preservative, water, etc. can be blended thereinto.

In the perfume of the present invention, a solvent, water, etc. can be blended thereinto in addition to 4(3)-(4-hydroxy-4-methylpentyl)-3-cyclohexene-1-carbonitrile of the present invention or a fragrance composition containing 4(3)-(4-hydroxy-4-methylpentyl)-3-cyclohexene-1-carbonitrile.

As described above, 4(3)-(4-hydroxy-4-methylpentyl)-3-cyclohexene-1-carbonitrile has a muguet odor and a citrus odor and can provide a bright muguet odor with good fragrance retention by further being blended with another fragrance. Therefore, as described above, the present invention provides a method of using 4(3)-(4-hydroxy-4-methylpentyl)-3-cyclohexene-1-carbonitrile as a fragrance component for a fragrance composition, a cleanser composition, a cosmetic, or a softener composition. The cleanser composition is preferably a body cleanser composition, a cleanser composition for clothing, or a cleanser composition for hard surfaces, more preferably a body cleanser composition or a cleanser composition for clothing, and further preferably a cleanser composition for clothing. Examples of the body cleanser composition include a skin cleanser composition and a hair cleanser composition, and it is preferably the skin cleanser composition. Examples of the cleanser composition for hard surfaces include an all purpose cleanser and a cleanser composition for tableware. The above-mentioned cosmetic is preferably a perfume.

In the aforementioned method of using 4(3)-(4-hydroxy-4-methylpentyl)-3-cyclohexene-1-carbonitrile, the amount of 4(3)-(4-hydroxy-4-methylpentyl)-3-cyclohexene-1-carbonitrile to be used is preferably 0.01 to 99 mass %, more preferably 0.1 to 50 mass %, and further preferably 0.3 to 25 mass %, with respect to the whole fragrance composition. When 4(3)-(4-hydroxy-4-methylpentyl)-3-cyclohexene-1-carbonitrile is used in an amount of 0.01 to 99 mass %, the fragrance composition can be provided with a bright muguet odor with good fragrance retention.

In the aforementioned method of using 4(3)-(4-hydroxy-4-methylpentyl)-3-cyclohexene-1-carbonitrile, 4(3)-(4-hydroxy-4-methylpentyl)-3-cyclohexene-1-carbonitrile is used for a cleanser composition, a cosmetic, or a softener composition in an amount of preferably 0.01 to 99 mass %, more preferably 0.1 to 50 mass %, and further preferably 0.3 to 25 mass %. When 4(3)-(4-hydroxy-4-methylpentyl)-3-cyclohexene-1-carbonitrile is used in an amount of 0.01 to 99 mass %, a cleanser composition, a cosmetic, or a softener composition can be provided with a bright muguet odor with good fragrance retention.

In the aforementioned method of using 4(3)-(4-hydroxy-4-methylpentyl)-3-cyclohexene-1-carbonitrile, a fragrance composition in which 4(3)-(4-hydroxy-4-methylpentyl)-3-cyclohexene-1-carbonitrile is used as a fragrance component may contain an oil which itself has no odor. The oil is the same as that described with respect to the above-mentioned fragrance composition. Furthermore, in the aforementioned method of using 4(3)-(4-hydroxy-4-methylpentyl)-3-cyclohexene-1-carbonitrile, a fragrance composition in which 4(3)-(4-hydroxy-4-methylpentyl)-3-cyclohexene-1-carbonitrile is used as a fragrance component may contain, as another fragrance, another fragrance component that is generally used or a blended fragrance having a desired composition in addition to 4(3)-(4-hydroxy-4-methylpentyl)-3-cyclohexene-1-carbonitrile. Such another fragrance is the same as that described with respect to the above-mentioned fragrance composition.

In the aforementioned method of using 4(3)-(4-hydroxy-4-methylpentyl)-3-cyclohexene-1-carbonitrile, a cleanser composition, a cosmetic, or a softener composition in which 4(3)-(4-hydroxy-4-methylpentyl)-3-cyclohexene-1-carbonitrile is used as a fragrance component may contain an oil which itself has no odor. The oil is the same as that described with respect to the above-mentioned fragrance composition. Furthermore, in the aforementioned method of using 4(3)-(4-hydroxy-4-methylpentyl)-3-cyclohexene-1-carbonitrile, a cleanser composition, a cosmetic, or a softener composition in which 4(3)-(4-hydroxy-4-methylpentyl)-3-cyclohexene-1-carbonitrile is used as a fragrance component may contain, as another fragrance, another fragrance component that is generally used or a blended fragrance having a desired composition in addition to 4(3)-(4-hydroxy-4-methylpentyl)-3-cyclohexene-1-carbonitrile. Such another fragrance is the same as that described with respect to the above-mentioned fragrance composition.

With respect to the above-described embodiment, the present invention further discloses 4(3)-(4-hydroxy-4-methylpentyl)-3-cyclohexene-1-carbonitrile and a method of producing 4(3)-(4-hydroxy-4-methylpentyl)-3-cyclohexene-1-carbonitrile.

<1> 4(3)-(4-Hydroxy-4-methylpentyl)-3-cyclohexene-1-carbonitrile.

<2> 4(3)-(4-Hydroxy-4-methylpentyl)-3-cyclohexene-1-carbonitrile according to the item <1>, wherein 4(3)-(4-hydroxy-4-methylpentyl)-3-cyclohexene-1-carbonitrile is a mixture of 4-(4-hydroxy-4-methylpentyl)-3-cyclohexene-1-carbonitrile and 3-(4-hydroxy-4-methylpentyl)-3-cyclohexene-1-carbonitrile.

<3> A fragrance composition, containing 4(3)-(4-hydroxy-4-methylpentyl)-3-cyclohexene-1-carbonitrile.

<4> The fragrance composition according to the item <3>, wherein the amount of 4(3)-(4-hydroxy-4-methylpentyl)-3-cyclohexene-1-carbonitrile to be contained in the fragrance composition is 0.01 to 99 mass %, preferably 0.1 to 15 mass %, and more preferably 0.3 to 3 mass %.

<5> The fragrance composition according to the item <3> or <4>, further containing a fragrance in addition to 4(3)-(4-hydroxy-4-methylpentyl)-3-cyclohexene-1-carbonitrile.

<6> The fragrance composition according to the item <5>, wherein the fragrance contained in addition to 4(3)-(4-hydroxy-4-methylpentyl)-3-cyclohexene-1-carbonitrile contains at least one selected from hydrocarbons, alcohols, phenols, aldehydes, ketones, acetals, ethers, esters, carbonates, lactones, oximes, nitriles, Schiff bases, nitrogen-containing compounds, sulfur-containing compounds, natural essential oils, and natural extracts.

<7> A cleanser composition, containing a fragrance composition according to any one of the items <3> to <6>.

<8> A cosmetic, containing a fragrance composition according to any one of the items <3> to <6>.

<9> A softener composition, containing a fragrance composition according to any one of the items <3> to <6>.

<10> A method of using 4(3)-(4-hydroxy-4-methylpentyl)-3-cyclohexene-1-carbonitrile as a fragrance component for a fragrance composition, a cleanser composition, a cosmetic, or a softener composition.

<11> The method according to the item <10>, wherein with respect to the whole of the fragrance composition, the cleanser composition, the cosmetic, or the softener composition, 4(3)-(4-hydroxy-4-methylpentyl)-3-cyclohexene-1-carbonitrile is used in an amount of preferably 0.01 to 99 mass %, more preferably 0.1 to 50 mass %, and further preferably 0.3 to 25 mass %.

<12> A method for producing 4(3)-(4-hydroxy-4-methylpentyl)-3-cyclohexene-1-carbonitrile, including a dehydration step of dehydrating 4(3)-(4-hydroxy-4-methylpentyl)-3-cyclohexene-1-carboxaldehyde oxime to yield 4(3)-(4-hydroxy-4-methylpentyl)-3-cyclohexene-1-carbonitrile.

<13> The method for producing 4(3)-(4-hydroxy-4-methylpentyl)-3-cyclohexene-1-carbonitrile according to the item <12>, wherein the dehydration step is carried out by an acetic anhydride method using acetic anhydride or an alkali catalyst method using alkali.

<14> The method for producing 4(3)-(4-hydroxy-4-methylpentyl)-3-cyclohexene-1-carbonitrile according to the item <13>, wherein the dehydration step is carried out by the alkali catalyst method in which 4(3)-(4-hydroxy-4-methylpentyl)-3-cyclohexene-1-carboxaldehyde oxime (an oxime intermediate) is dehydrated by heating in the presence of an alkali catalyst (preferably, alkali metal hydroxide such as sodium hydroxide or potassium hydroxide) to yield 4(3)-(4-hydroxy-4-methylpentyl)-3-cyclohexene-1-carbonitrile.

<15> The method for producing 4(3)-(4-hydroxy-4-methylpentyl)-3-cyclohexene-1-carbonitrile according to the item <14>, wherein the amount of the alkali catalyst to be used is, with respect to the oxime intermediate, 0.1 to 20 mass %, preferably 1 to 15 mass %.

<16> The method for producing 4(3)-(4-hydroxy-4-methylpentyl)-3-cyclohexene-1-carbonitrile according to the item <14> or <15>, wherein the alkali catalyst method is performed, with a reaction being carried out while by-product water is removed out of the system, and is performed preferably by an azeotropic dehydration method under solvent reflux or by a continuous dehydration method in which a product also is removed out of the reaction system.

<17> The method for producing 4(3)-(4-hydroxy-4-methylpentyl)-3-cyclohexene-1-carbonitrile according to any one of the items <12> to <16>, wherein 4(3)-(4-hydroxy-4-methylpentyl)-3-cyclohexene-1-carboxaldehyde oxime (an oxime intermediate) is obtained by oximating 4(3)-(4-hydroxy-4-methylpentyl)-3-cyclohexene-1-carboxaldehyde.

<18> The method for producing 4(3)-(4-hydroxy-4-methylpentyl)-3-cyclohexene-1-carbonitrile according to the item <17>, wherein the oximating is carried out by a method in which a hydroxylamine aqueous solution is dropped into 4(3)-(4-hydroxy-4-methylpentyl)-3-cyclohexene-1-carboxaldehyde or a method in which a base (preferably, alkali metal hydroxide such as sodium hydroxide or potassium hydroxide) is dropped into a mixture of 4(3)-(4-hydroxy-4-methylpentyl)-3-cyclohexene-1-carboxaldehyde and an aqueous solution of inorganic acid salt of hydroxylamine (preferably, hydroxylamine sulfate).

<19> The method for producing 4(3)-(4-hydroxy-4-methylpentyl)-3-cyclohexene-1-carbonitrile according to the item <18>, wherein the amount of the hydroxylamine or inorganic acid salt thereof to be used is, in terms of hydroxylamine, 1.0 to 3.0 times by mole, preferably 1.0 to 2.0 times by mole, and more preferably 1.0 to 1.5 times by mole, with respect to 4(3)-(4-hydroxy-4-methylpentyl)-3-cyclohexene-1-carboxaldehyde.

EXAMPLES

The following examples further describe and demonstrate embodiments of the present invention. The examples are given solely for the purpose of illustration and are not to be construed as limitations of the present invention.

Details of the measurement methods carried out in the following examples and comparative examples are described together below.

Details of the measurement methods carried out in the following production example are described together below.

[Conversion Ratio and Yield]

The conversion ratio and the yield described in the following production example were determined by an internal standard method of gas chromatography (GC) quantitative analysis.

<Apparatus and Analytical Conditions for Gas Chromatography>

GC Apparatus: HP6850, manufactured by HEWLETT PACKARD

Column: DB-1 (Inner Diameter: 0.25 mm, Length: 30 m, and Film Thickness: 0.25 μm), manufactured by J&W Carrier Gas: He, 1.5 mL/min Injection Condition: 280° C., Split Ratio: 1/100

Detection Condition: FID System, 280° C.

Column Temperature Condition: 100° C.→Raised at 6° C./min→Maintained at 300° C. for 10 minutes Internal Standard Compound: n-Dodecane

[Compound Identification]

Each compound obtained in the following production example was identified by spectrum analyses using a nuclear magnetic resonance spectrum (Mercury 400, manufactured by Varian) ($^{1}$H-NMR, $^{13}$C-NMR), a Fourier transform infrared spectrophotometer (FT-710, manufactured by HORIBA, Ltd.), and a gas chromatography mass spectrometer (GC-MS) (GC-2010, manufactured by Shimadzu Corporation). The measurement conditions, etc. are described in each measurement result.

[Odor Evaluation]

Two experts who had an experience of at least five years but less than ten years as well as three experts who had an experience of at least 25 years of blending odors and evaluating fragrances determined the fragrance note and the intensity by a smelling strip method. About 5 mm of the end of each smelling strip (fragrance test paper with a width of 6 mm and a length of 150 mm) was immersed in a sample and thereby evaluation was performed.

With respect to the odor, fragrances that are sensed mainly (main odors) were listed from the strongest to the weakest and further fragrances that are sensed secondarily (secondary odors) were noted.

The odor intensity was indicated by the relative evaluation, with 0 denoting odorless and 5 denoting very strong, and the evaluation result was obtained, with the result being rounded off to the nearest whole number.

Production Example 1

Production of 4(3)-(4-hydroxy-4-methylpentyl)-3-cyclohexene-1-carboxaldehyde oxime

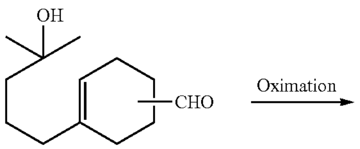

4(3)-(4-Hydroxy-4-methylpentyl)-3-cyclohexene-1-carboxaldehyde (III)

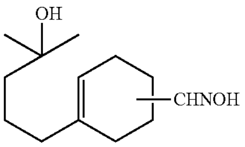

4(3)-(4-Hydroxy-4-methylpentyl)-3-cyclohexene-1-carboxaldehyde oxime (II)

In a 200 mL flask, 32 g of 4(3)-(4-hydroxy-4-methylpentyl)-3-cyclohexene-1-carboxaldehyde (Lyral, Trade Name of IFF, 0.15 mole), 30 g of isopropyl alcohol, 19 g of hydroxylamine sulfate (0.11 mole, 0.73 times by mole with respect to aldehyde and 1.46 times by mole in terms of hydroxylamine), and 35 g of ion exchanged water were added sequentially. This was heated to 45° C. while being stirred in a nitrogen atmosphere. While the reaction temperature was kept at 40 to 50° C., 33 g (0.25 mole) of 30 mass % sodium hydroxide aqueous solution was dropped over 30 minutes. Further, heating and stirring were continued for one hour. After the reaction solution was cooled to room temperature, an aqueous layer was extracted by settled separation. An organic layer was washed with a 10 mass % sodium sulfate aqueous solution and then isopropyl alcohol was distilled, which yielded 39 g of a pale yellow liquid product. As a result of gas chromatography quantitative analysis of the product, 4(3)-(4-hydroxy-4-methylpentyl)-3-cyclohexene-1-carboxaldehyde had an conversion ratio of 100% and 4(3)-(4-hydroxy-4-methylpentyl)-3-cyclohexene-1-carboxaldehyde oxime had a purity of 75% and a yield of 87%. Furthermore, 4(3)-(4-hydroxy-4-methylpentyl)-3-cyclohexene-1-carboxaldehyde oxime was a mixture of two types, i.e., a main component and an accessory component. The mixing ratio of the main component and the accessory component was 3:1 (the main component:the accessory component). The mixture of the two types, i.e., the main component and the accessory component, was a mixture of 4-(4-hydroxy-4-methylpentyl)-3-cyclohexene-1-carboxaldehyde oxime (a compound of Formula (IIA)) and 3-(4-hydroxy-4-methylpentyl)-3-cyclohexene-1-carboxaldehyde oxime (a compound of Formula (IIB)). Therefore, either the main component or the accessory component is the compound of Formula (IIA) described above and the other is the compound of Formula (IIB) described above.

The measurement results of each spectrum analysis and odor evaluation are indicated below.

(1) MS (the EI method); m/z: 255 ($M^+$), 190, 174, 162, 146, 133, 119, 106, 91, 79, 59, 41

(2) $^{1}$H-NMR ($CDCl_3$, 400 MHz); δ (ppm):

Main Component: 1.12-1.31 (2H, m), 1.21 (6H, s), 1.38-1.50 (3H, m), 1.78-1.91 (2H, m), 1.92-2.10 (4H, m), 2.13-2.26 (1H, m), 2.42-2.54 (1H, m), 5.37-5.43 (1H, m), 7.38 (1H, d, J=6.0 Hz), 8.64 (1H, s)

Accessory Component: 1.12-1.31 (2H, m), 1.44 (6H, s), 1.52-1.61 (3H, m), 1.62-1.79 (2H, m), 1.92-2.10 (4H, m), 2.13-2.26 (1H, m), 3.17-3.22 (1H, m), 5.37-5.43 (1H, m), 6.60 (1H, d, J=7.2 Hz), 9.02 (1H, s)

(3) $^{13}$C-NMR ($CDCl_3$, 100 MHz); δ (ppm):

Main Component: 22.8, 26.0, 29.2, 29.5, 29.6, 34.9, 38.4, 43.7, 71.5, 119.2, 137.7, 155.3

Accessory Component: 22.8, 26.6, 29.4, 29.5, 29.6, 35.2, 38.5, 43.8, 71.5, 120.9, 137.8, 155.3

(4) FT-IR (neat); $cm^{-1}$: 3275 (br), 2966, 2933, 2837, 2366, 1649, 1437, 1365, 1201, 1149

(5) Odor: Main Odor: Floral (Lily)

(6) Odor Intensity: 1

Example 1

Production of 4(3)-(4-hydroxy-4-methylpentyl)-3-cyclohexene-1-carbonitrile

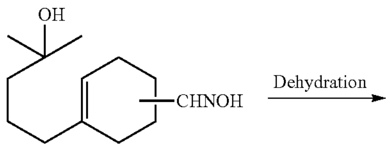

4(3)-(4-Hydroxy-4-methylpentyl)-3-cyclohexene-1-carboxyaldehyde oxime (II)

-continued

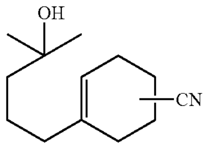

4(3)-(4-Hydroxy-4-methylpentyl)-3-cyclohexene-1-carbonitrile
(I)

In a 300 mL flask with a Dean-Stark dehydration tube attached thereto, 35 g of 4(3)-(4-hydroxy-4-methylpentyl)-3-cyclohexene-1-carboxaldehyde oxime (the crude product of Production Example 1, with a pure content of 26 g, 0.12 mole), 3.0 g of powdered sodium hydroxide (75 mmoles, 8.6 mass % with respect to the oxime intermediate), and 100 g of toluene were placed, which then was refluxed continuously for three hours until water distillate stopped coming out. After the reactant was cooled to room temperature, 50 g of water was added thereto to dissolve sodium hydroxide, which then was further neutralized with acetic acid. An aqueous layer was extracted by settled separation. Further, an organic layer was washed twice with a 10 mass % sodium sulfate aqueous solution and then toluene was distilled, which yielded 33 g of an orange liquid product. As a result of gas chromatography quantitative analysis of the product, 4(3)-(4-hydroxy-4-methylpentyl)-3-cyclohexene-1-carboxaldehyde oxime had a conversion ratio of 72% and 4(3)-(4-hydroxy-4-methylpentyl)-3-cyclohexene-1-carbonitrile had a purity of 51% and a yield of 70%.

Then 30 g of this crude product was subjected to vacuum distillation purification and thereby a pale yellow liquid that was distilled at 166 to 172° C./70 Pa was obtained. 4(3)-(4-Hydroxy-4-methylpentyl)-3-cyclohexene-1-carbonitrile had a purity of 90%. Furthermore, 4(3)-(4-hydroxy-4-methylpentyl)-3-cyclohexene-1-carbonitrile was a mixture of two types, i.e. a main component and an accessory component, and the mixing ratio of the main component and the accessory component was 3:1 (the main component:the accessory component). The mixture of two types, i.e. the main component and the accessory component, was a mixture of 4-(4-hydroxy-4-methylpentyl)-3-cyclohexene-1-carbonitrile (a compound of Formula (IA)) and 3-(4-hydroxy-4-methylpentyl)-3-cyclohexene-1-carbonitrile (a compound of (Formula (IB)). Therefore, either the main component or the accessory component is the compound of Formula (IA) described above and the other is the compound of Formula (IB) described above.

The measurement results of each spectrum analysis and odor evaluation are indicated below.

(1) MS (the EI method); m/z: 270 ($M^+$), 189, 174, 161, 146, 133, 118, 106, 91, 79, 59, 41

(2) $^1$H-NMR ($CDCl_3$, 400 MHz); δ (ppm):

Main Component: 1.13-1.26 (2H, m), 1.20 (6H, s), 1.40-1.46 (2H, m), 1.91-2.03 (4H, m), 2.12-2.40 (4H, m), 2.75-2.86 (1H, m), 5.35 (1H, br.s)

Accessory Component: 1.13-1.24 (2H, m), 1.43 (6H, s), 1.39-1.51 (2H, m), 1.77-2.02 (5H, m), 2.12-2.40 (4H, m), 5.46 (1H, br.s)

(3) $^{13}$C-NMR ($CDCl_3$, 100 MHz); δ (ppm):

Main Component: 22.5, 25.1, 25.6, 26.3, 29.5, 31.5, 38.0, 43.6, 71.1, 117.4, 122.7, 138.0.

Accessory Component: 23.3, 25.5, 26.0, 28.7, 29.5, 29.6, 38.2, 43.6, 71.1, 120.9, 122.8, 134.3

(3) FT-IR (neat); $cm^{-1}$: 3371 (br), 2966, 2935, 2233, 1466, 1379, 1130, 951

(4) Odor: Main Odor: Floral (Muguet); Secondary Odor: Citrus (5) Odor Intensity: 3

Example 2 and Comparative Examples 1 to 3

Fragrance Composition for Liquid Detergent

Using 4(3)-(4-hydroxy-4-methylpentyl)-3-cyclohexene-1-carbonitrile obtained in Example 1, a fragrance was prepared in such a manner as to have a mixed composition indicated in Table 1. Thus a fragrance composition of Example 2 was obtained. Furthermore, in the same manner as in Example 2, fragrance compositions were obtained, as Comparative Example 1 and Comparative Example 2, in which Lyral (4(3)-(4-hydroxy-4-methylpentyl)-3-cyclohexene-1-carboxaldehyde) manufactured by IFF and Azuril (4(3)-(4-methyl-3-pentenyl)-3-cyclohexene-1-carbonitrile) manufactured by Innospec were used, respectively, instead of 4(3)-(4-hydroxy-4-methylpentyl)-3-cyclohexene-1-carbonitrile of Example 2. Moreover, as Comparative Example 3, a fragrance composition was obtained in which dipropylene glycol (a solvent) was used instead of 4(3)-(4-hydroxy-4-methylpentyl)-3-cyclohexene-1-carbonitrile of Example 2.

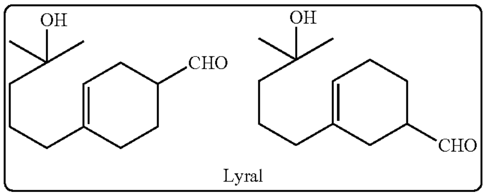

Lyral

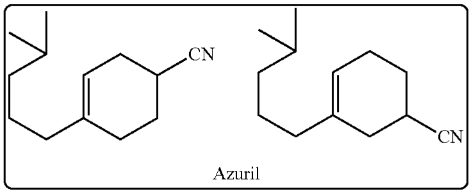

Azuril

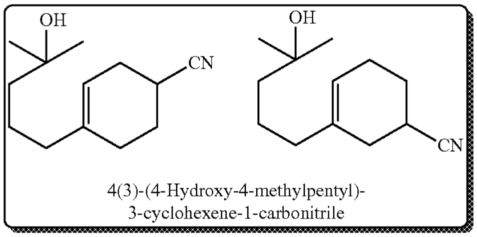

4(3)-(4-Hydroxy-4-methylpentyl)-3-cyclohexene-1-carbonitrile

TABLE 1

| | (Unit: Part by Mass) Ex. 2 | C. Ex. 1 | C. Ex. 2 | C. Ex. 3 |
|---|---|---|---|---|
| Aldehyde C-12MNA (Trade Name of Kao Corporation)[1] | 25 | 25 | 25 | 25 |
| Ambrotech (Trade Name of Kao Corporation)[2] | 10 | 10 | 10 | 10 |
| Benzyl acetone | 20 | 20 | 20 | 20 |
| Coumarin | 10 | 10 | 10 | 10 |
| β-Damascone | 5 | 5 | 5 | 5 |
| Dihydromyrcenol | 100 | 100 | 100 | 100 |
| Diphenyl oxide | 10 | 10 | 10 | 10 |
| Ethyl 2-methylbutyrate 10% | 10 | 10 | 10 | 10 |
| Geranium synth | 50 | 50 | 50 | 50 |
| Hexyl salicylate | 220 | 220 | 220 | 220 |
| Iso E Super (Trade Name of IFF)[3] | 120 | 120 | 120 | 120 |
| γ-Methylionone | 75 | 75 | 75 | 75 |
| Methyl nonyl ketone 10% | 10 | 10 | 10 | 10 |
| Peonile (Trade Name of Givaudan)[4] | 80 | 80 | 80 | 80 |
| Rosemary oil | 35 | 35 | 35 | 35 |
| Tricyclodecenyl acetate | 50 | 50 | 50 | 50 |
| Triplal (Trade Name of IFF)[5] | 15 | 15 | 15 | 15 |
| γ-Undecalactone (Trade Name of Kao Corporation) | 15 | 15 | 15 | 15 |
| Undecavertol (Trade Name of Givaudan)[6] | 20 | 20 | 20 | 20 |
| Lyral (Trade Name of IFF)[7] | 0 | 120 | 0 | 0 |
| Azuril (Trade Name of Innospec)[8] | 0 | 0 | 120 | 0 |
| 4(3)-(4-Hydroxy-4-methylpentyl)-3-cyclohexene-1-carbonitrile (Compound of the present invention) | 120 | 0 | 0 | 0 |
| Dipropylene glycol | 0 | 0 | 0 | 120 |
| Total | 1000 | 1000 | 1000 | 1000 |

[1]Trade Name of Kao Corporation, 2-Methyl-undecanal
[2]Trade Name of Kao Corporation, Dodecahydro-3a,6,6,9a-tetramethyl naphto[2,1-b]furan
[3]Trade Name of IFF, 1-(1,2,3,4,5,6,7,8-Octahydro-2,3,8,8-tetramethyl-2-naphthalenyl)-ethan-1-one
[4]Trade Name of Givaudan, 2-Cyclohexylidene-2-phenylacetonitrile
[5]Trade Name of IFF, 2,4-Dimethyl-3-cyclohexene-1-carboxaldehyde
[6]Trade Name of Givaudan, 4-Methyl-3-decene-5-ol
[7]Trade Name of IFF, 4(3)-(4-Hydroxy-4-methylpentyl)-3-cyclohexene-1-carboxaldehyde
[8]4(3)-(4-Methyl-3-pentenyl)-3-cyclohexene-1-carbonitrile, manufactured by Innospec The evaluation was performed in the same manner as in the aforementioned odor evaluation.

The fragrance composition of Example 2 had a muguet-like odor with enhanced brightness and had improved fragrance retention as compared to the fragrance compositions of Comparative Examples 1 to 3. On the other hand, the fragrance composition of Comparative Example 1 had a voluminous muguet-like odor but was poor in brightness. The fragrance composition of Comparative Example 2 had a green ozone-like fresh odor. The fragrance composition of Comparative Example 3 had a floral aldehyde green-like odor, in which the aldehyde green-like odor was stronger than the floral.

Example 4 and Comparative Example 4

Cleanser Composition for Clothing

To a non-fragranced liquid cleanser for clothing having the composition indicated in Table 2, each of the fragrance compositions obtained in Example 2 and Comparative Example 3 was added to be contained in an amount of 0.4 mass %. Thus, cleanser compositions of Example 4 and Comparative Example 4 were prepared, respectively.

TABLE 2

| Non-fragranced liquid cleanser for clothing | Blended Amount (mass %) |
|---|---|
| Sodium polyoxyethylene(2)lauryl ether sulfate[1] | 9.1 |
| Polyethoxyethylenated alcohol[2] | 6.4 |
| Linear fatty acid[3] | 2.9 |
| Citric acid | 3.0 |
| 50% sodium hydroxide | 2.8 |
| Ethanol | 1.0 |
| Preservative[4] | 0.15 |
| Sodium chloride | Suitable Amount |
| Ion exchanged water | Remainder |
| pH | 8.3 |

[1]Emal 270E (Trade Name of Kao Corporation)
[2]Findet 1315/19CP (Trade Name of Kao Corporation)
[3]Prifac 7901 (Trade Name of Uniqema)
[4]Mirecide NB/70 (Trade Name of Lamirsa)

The cleanser composition of Example 4 had a brighter muguet-like odor as compared to the cleanser composition of Comparative Example 4.

INDUSTRIAL APPLICABILITY

Since 4(3)-(4-hydroxy-4-methylpentyl)-3-cyclohexene-1-carbonitrile of the present invention has a citrus odor in addition to a muguet odor, which is useful as a fragrance, it can be used as a fragrance material. Furthermore, it is stable in an aqueous vehicle. Moreover, 4(3)-(4-hydroxy-4-methylpentyl)-3-cyclohexene-1-carbonitrile of the present invention also can provide a bright muguet odor with good fragrance retention by being blended with another fragrance. Thus, the fragrance composition containing 4(3)-(4-hydroxy-4-methylpentyl)-3-cyclohexene-1-carbonitrile of the present invention can be used as a fragrance component for a cleanser composition, a cosmetic, etc.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. 4(3)-(4-hydroxy-4-methylpentyl)-3-cyclohexene-1-carbonitrile.

2. 4(3)-(4-Hydroxy-4-methylpentyl)-3-cyclohexene-1-carbonitrile according to claim 1, wherein 4(3)-(4-hydroxy-4-methylpentyl)-3-cyclohexene-1-carbonitrile is a mixture of 4-(4-hydroxy-4-methylpentyl)-3-cyclohexene-1-carbonitrile and 3-(4-hydroxy-4-methylpentyl)-3-cyclohexene-1-carbonitrile.

3. A fragrance composition comprising 4(3)-(4-hydroxy-4-methylpentyl)-3-cyclohexene-1-carbonitrile.

4. The fragrance composition according to claim 3, wherein 4(3)-(4-hydroxy-4-methylpentyl)-3-cyclohexene-1-carbonitrile is a mixture of 4-(4-hydroxy-4-methylpentyl)-3-cyclohexene-1-carbonitrile and 3-(4-hydroxy-4-methylpentyl)-3-cyclohexene-1-carbonitrile.

5. The fragrance composition according to claim 4, wherein when either 4-(4-hydroxy-4-methylpentyl)-3-cyclohexene-1-carbonitrile or the 3-(4-hydroxy-4-methylpentyl)-3-cyclohexene-1-carbonitrile is considered as a main component while the other is considered as an accessory component, the ratio between the main component and the accessory component is 1 to 100:1.

6. The fragrance composition according to claim 3, wherein the amount of 4(3)-(4-hydroxy-4-methylpentyl)-3-cyclohexene-1-carbonitrile to be contained in the fragrance composition is 0.01 to 99 mass %.

7. The fragrance composition according to claim 3, wherein the amount of 4(3)-(4-hydroxy-4-methylpentyl)-3-cyclohexene-1-carbonitrile to be contained in the fragrance composition is 0.1 to 15 mass %.

8. The fragrance composition according to claim 3, wherein the amount of 4(3)-(4-hydroxy-4-methylpentyl)-3-cyclohexene-1-carbonitrile to be contained in the fragrance composition is 0.3 to 3 mass %.

9. The fragrance composition according to claim 3 further comprising a fragrance in addition to 4(3)-(4-hydroxy-4-methylpentyl)-3-cyclohexene-1-carbonitrile.

10. The fragrance composition according to claim 9, wherein the fragrance contained in addition to 4(3)-(4-hydroxy-4-methylpentyl)-3-cyclohexene-1-carbonitrile contains at least one selected from hydrocarbons, alcohols, phenols, aldehydes, ketones, acetals, ethers, esters, carbonates, lactones, oximes, nitriles, Schiff bases, nitrogen-containing compounds, sulfur-containing compounds, natural essential oils, and natural extracts.

11. The fragrance composition according to claim 9, wherein the fragrance contained in addition to 4(3)-(4-hydroxy-4-methylpentyl)-3-cyclohexene-1-carbonitrile contains at least one selected from alcohols, aldehydes, ketones, ethers, esters, lactones, and natural essential oils.

12. The fragrance composition according to claim 9, wherein the amount of the fragrance to be contained in addition to 4(3)-(4-hydroxy-4-methylpentyl)-3-cyclohexene-1-carbonitrile is 0.0001 to 99.99 mass %.

13. The fragrance composition according to claim 9 further comprising an oil.

14. A cleanser composition comprising a fragrance composition according to claim 3.

15. The cleanser composition according to claim 14 further comprising an anionic surfactant.

16. The cleanser composition according to claim 14, wherein the cleanser composition is a body cleanser composition, a cleanser composition for clothing, or a cleanser composition for hard surfaces.

17. The cleanser composition according to claim 14, wherein the cleanser composition is a cleanser composition for clothing.

18. A cosmetic comprising a fragrance composition according to claim 3.

19. A softener composition comprising a fragrance composition according to claim 3.

* * * * *